(12) United States Patent
Van Der Kerken et al.

(10) Patent No.: US 8,047,845 B2
(45) Date of Patent: Nov. 1, 2011

(54) DENTAL PROSTHESIS STABILIZER

(75) Inventors: Andre Jozef Ernest Van Der Kerken, Kapellen (BE); Pieter Van Der Veken, Mortsel (BE)

(73) Assignee: Group Vander Kerken Van der Veken (BE)

( * ) Notice: Subject to any disclaimer, the term of this patent is extended or adjusted under 35 U.S.C. 154(b) by 573 days.

(21) Appl. No.: 12/063,549

(22) PCT Filed: Jun. 30, 2006

(86) PCT No.: PCT/BE2006/000075
§ 371 (c)(1),
(2), (4) Date: Feb. 11, 2008

(87) PCT Pub. No.: WO2007/016753
PCT Pub. Date: Feb. 15, 2007

(65) Prior Publication Data
US 2010/0178635 A1 Jul. 15, 2010

(30) Foreign Application Priority Data

Aug. 11, 2005 (BE) .................................. 2005/0391

(51) Int. Cl.
*A61C 13/38* (2006.01)
(52) U.S. Cl. ....................................................... 433/179
(58) Field of Classification Search .......... 433/177–179, 433/171, 196, 199.1, 229, 49, 52–54, 57–58, 433/60–69; 623/17.17, 18.11
See application file for complete search history.

(56) References Cited

U.S. PATENT DOCUMENTS

| | | | | |
|---|---|---|---|---|
| 5,181 A * | 7/1847 | Stuart | ............. | 433/179 |
| 2,224,511 A * | 12/1940 | Cleven | ............. | 433/179 |
| 2,610,402 A * | 9/1952 | Craigo | ............. | 433/71 |
| 2,680,908 A * | 6/1954 | Daigle | ............. | 433/136 |
| 4,382,783 A * | 5/1983 | Rosenberg | ............. | 433/19 |
| 4,451,234 A * | 5/1984 | Oye | ............. | 433/54 |
| 5,562,445 A * | 10/1996 | DeVincenzo et al. | ............. | 433/19 |
| 5,807,102 A * | 9/1998 | Lang et al. | ............. | 433/64 |
| 5,980,247 A * | 11/1999 | Cleary | ............. | 433/19 |
| 6,305,940 B1 * | 10/2001 | Vander Kerken et al. | ............. | 433/179 |
| 6,386,868 B1 * | 5/2002 | Fujita | ............. | 433/60 |
| 2004/0146829 A1 * | 7/2004 | Lopez | ............. | 433/57 |
| 2009/0317761 A1 * | 12/2009 | Van Der Veken et al. | ............. | 433/172 |

FOREIGN PATENT DOCUMENTS

| | | |
|---|---|---|
| BE | 1006478 | 9/1994 |
| BE | 1013039 | 8/2001 |
| DE | 2702315 | 7/1978 |
| EP | 0226962 | 7/1987 |
| EP | 1046380 | 10/2000 |

* cited by examiner

*Primary Examiner* — Cris L Rodriguez
*Assistant Examiner* — Hao D Mai
(74) *Attorney, Agent, or Firm* — The Webb Law Firm

(57) ABSTRACT

An improved dental prosthesis stabilizer includes two arms connected to each other by a hinge joint and with which an upper dental prosthesis and a lower dental prosthesis are coupled to one another. A spring is provided at the hinge joint with which the upper prosthesis and the lower prosthesis are pushed away from each other. At least one of the arms is telescopic and is formed of a bent distal end of the spring, which can be axially moved in a bent guide. The guide is fixed on the upper dental prosthesis or the lower dental prosthesis or is embedded therein.

6 Claims, 3 Drawing Sheets

Figure 3:
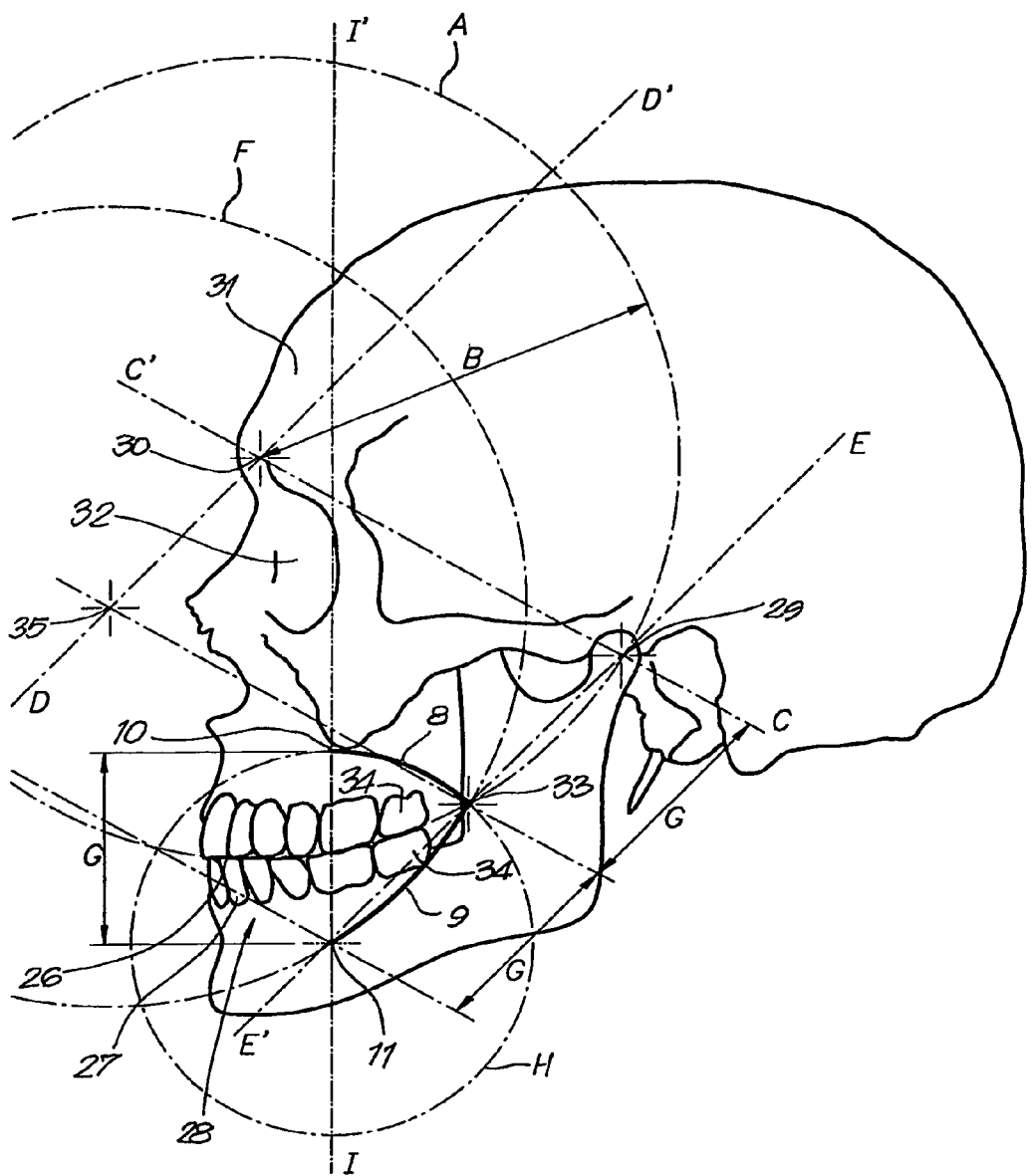

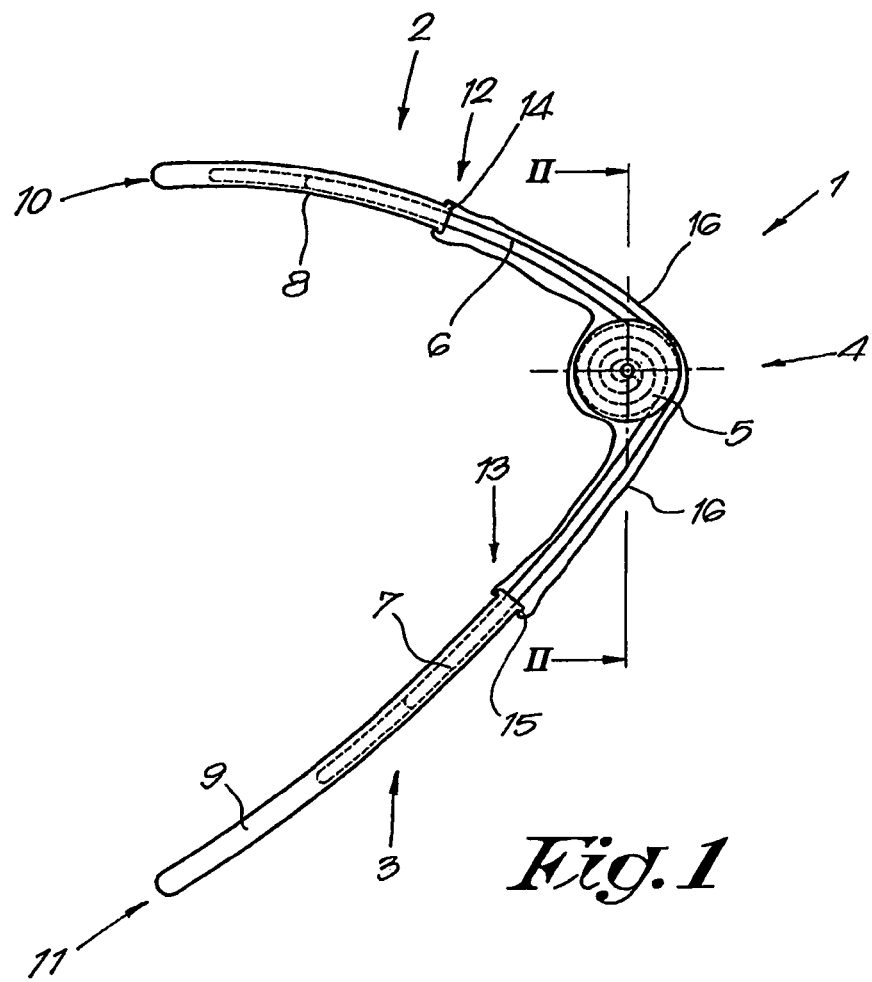
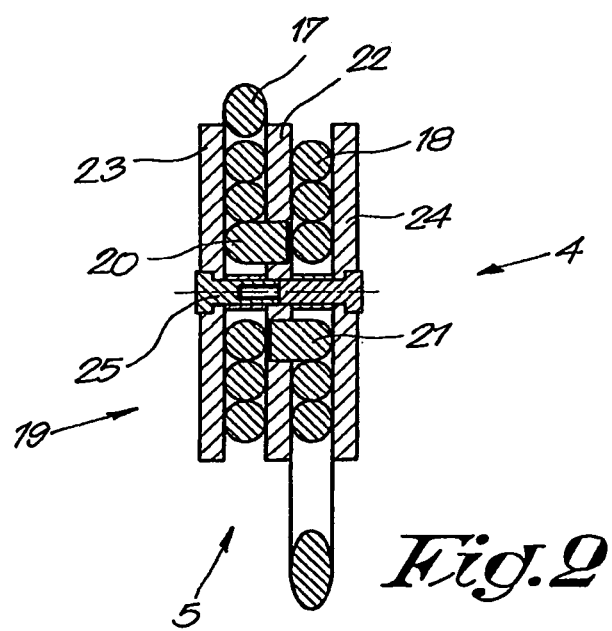

DENTAL PROSTHESIS STABILIZER

The present invention concerns an improved dental prosthesis stabilizer.

In particular, the present invention concerns a dental prosthesis stabilizer which is provided with two arms which are hinge-mounted to one another and with which an upper dental prosthesis and a lower dental prosthesis are coupled to each other, whereby a spring is provided at the hinge joint with which the upper prosthesis and the lower prosthesis are pushed away from each other.

Such dental prosthesis stabilizers are already known, for example from Belgian patent No. 1,006,478, whereby the springy hinge joint between the arms is situated at an invariable distance from the upper as well as the lower dental prosthesis and whereby the arms are hinge-mounted to the upper and the lower dental prosthesis by means of screws.

A disadvantage of these dental prosthesis stabilizers is that they cannot easily follow the natural movement of the jaws, as the hinge point of the dental prosthesis stabilizer, around which the upper and lower dental prostheses hinge in relation to each other, is necessarily situated in the oral cavity, whereas the natural movement of the teeth follows the jaws which hinge in relation to a point which is situated more in the back of the head.

This has for a result that prostheses, equipped with the above-mentioned dental prosthesis stabilizer, often come off the jaw.

Another disadvantage of such dental prosthesis stabilizers is that, if a part of the dental prosthesis stabilizer is worn or broken, such as for example when the spring breaks, the repair of such a dental prosthesis stabilizer causes a lot of inconveniences, as the dental prosthesis is usually given as a whole in the care of the dental technician during the repair period, since the dental prosthesis stabilizer cannot be disconnected from the dental prosthesis by an ordinary user.

A first improvement to the dental prosthesis stabilizers of the above-mentioned type is known from Belgian patent No. 09,900,277.

This improvement consists in making one of the arms of the dental prosthesis stabilizer telescopic, and in providing the other arm to a point of attachment in the form of a knob-shaped protrusion which can slide in a groove provided in the upper or lower prosthesis.

Thus is obtained much more freedom of movement for the above-mentioned hinge point between the upper and lower dental prosthesis, so that it becomes easier to follow the natural movement.

Further, this improvement also makes sure that the dental prosthesis stabilizer can be easily disconnected from the dental prosthesis by an ordinary user, but only when the dental prosthesis is taken out of the mouth.

A major disadvantage of the latter form of known dental prosthesis stabilizers, however, is that they consist of a large number of parts, which entails a rather large risk of failure.

Another disadvantage related to the known dental prosthesis stabilizers is that the parts are exposed to a rather aggressive environment, especially to all sorts of fluids and food in the mouth, as a result of which the parts are very liable to wear.

Further, leavings often stay behind the parts of the known dental prosthesis stabilizers, with all the accompanying discomforts for a result.

Further, it appears that some persons find it psychologically hard to wear any of the known dental prosthesis stabilizers, as they associate it with a horse bit because of the presence of visible metal parts of the dental prosthesis stabilizer.

The present invention aims to remedy one or several of the above-mentioned and other disadvantages.

To this end, the present invention concerns an improved dental prosthesis stabilizer which is provided with two arms which are connected to each other by means of a hinge joint and with which an upper dental prosthesis and a lower dental prosthesis are coupled to each other, whereby, at the hinge joint, a spring is provided with which the upper prosthesis and the lower prosthesis are pushed away from each other and whereby at least one of the arms is made telescopic and is formed of a bent far end of the above-mentioned spring, which can be axially moved in a bent guide, which guide is designed to be fixed on an upper dental prosthesis or a lower dental prosthesis or to be embedded therein.

An advantage of such a dental prosthesis stabilizer according to the invention is that it consists of far less parts than the known dental prosthesis stabilizers, so that the risk of failure of the dental prosthesis stabilizer is strongly reduced.

Another advantage of such a dental prosthesis stabilizer is that the above-mentioned guides can be easily worked into the upper and lower dental prosthesis, as a result of which the dental prosthesis stabilizer will be exposed less to aggressive chemical effects, and a dental prosthesis equipped with such a dental prosthesis stabilizer will be much more comfortable to wear.

According to a preferred embodiment of a dental prosthesis stabilizer according to the invention, both arms of the dental prosthesis stabilizer are made telescopic in the shape of a bent far end of the above-mentioned spring.

This embodiment provides even more freedom of movement to the hinge point.

According to another preferred embodiment of a dental prosthesis stabilizer according to the invention, the bent far end of the spring which is designed for the lower dental prosthesis has a curvature radius which corresponds to the curvature radius of what is called the curve of Spee of the set of teeth of the person for whom the dental prosthesis is meant.

This curve of Spee is a curve which follows the shape of the profile of the set of teeth, as will be described more clearly hereafter.

Additionally, the bent far end of the spring which is designed for the upper dental prosthesis and the accompanying guide preferably also have a curvature radius which is equal to the difference in distance between the hinge point of the dental prosthesis stabilizer and the maxillary joint of the person for whom the dental prosthesis is meant.

An advantage of these embodiments of a dental prosthesis stabilizer is that the bent far ends of the spring, when the jaws open and close, thanks to the above-mentioned shapes of the bent far ends and the accompanying guides, can perfectly slide in the guides concerned without suffering any noticeable friction.

According to yet another preferred embodiment of a dental prosthesis stabilizer according to the invention, the hinge and the spring are enveloped by a flexible capsule.

This embodiment is advantageous in that the person wearing such a dental prosthesis stabilizer does not or hardly feel the presence of the dental prosthesis stabilizer in the oral cavity, in that the dental prosthesis stabilizer is additionally protected against negative chemical influences and in that no leavings can stay behind parts of the dental prosthesis stabilizer.

Figure 4:
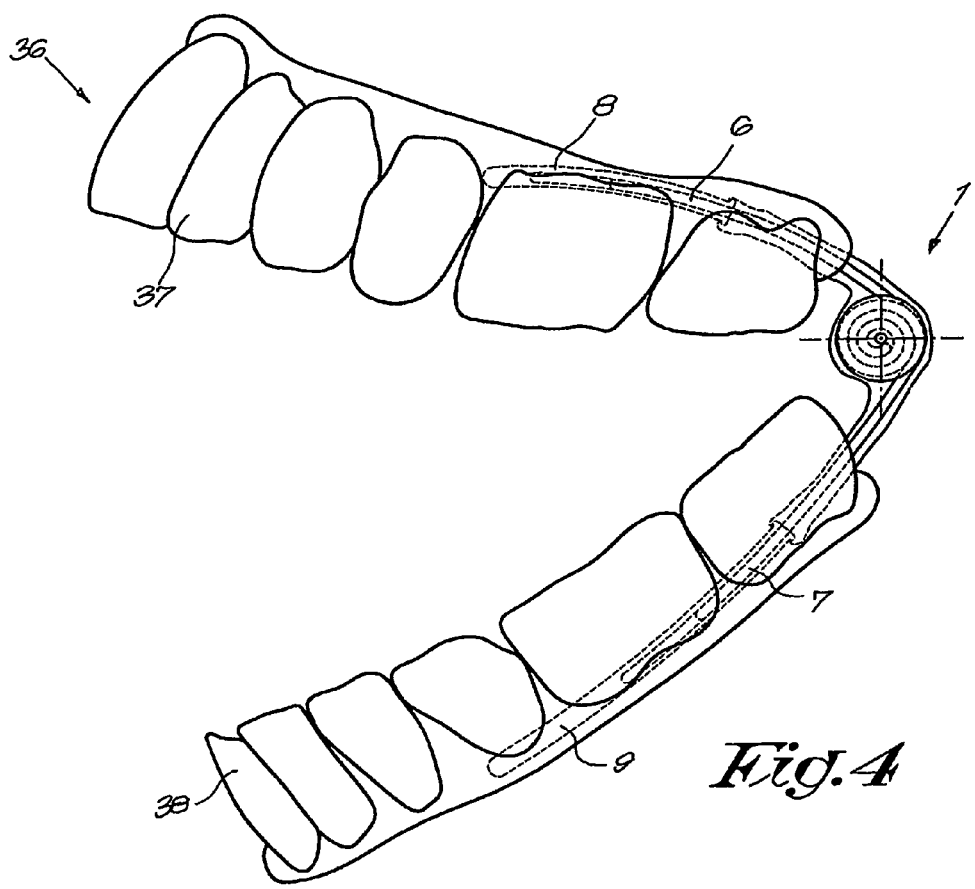
Figure 5:
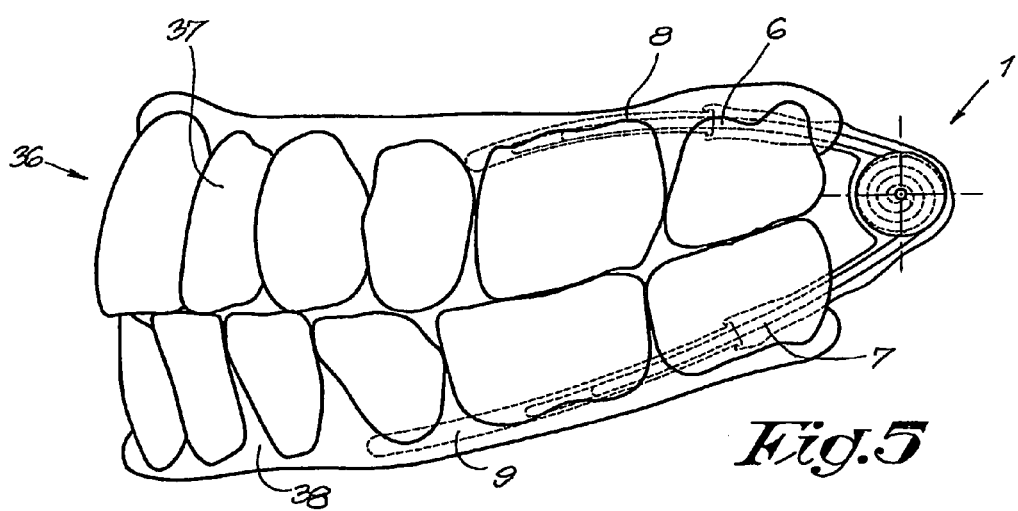

In order to better explain the characteristics of the invention, the following description of an improved dental prosthesis stabilizer according to the invention is given as an example only, without being limitative in any way, with reference to the accompanying drawings, in which:

FIG. 1 schematically represents a dental prosthesis stabilizer according to the invention;

FIG. 2 represents a section according to line II-II in FIG. 1 to a larger scale;

FIG. 3 schematically represents the geometry of the dental prosthesis stabilizer from FIG. 1 with reference to a skull;

FIGS. 4 and 5 represent the dental prosthesis stabilizer according to FIG. 1, applied to an upper and a lower dental prosthesis.

The improved dental prosthesis stabilizer 1 according to the invention, represented in FIGS. 1 and 2, mainly consists of two arms 2 and 3 which are connected to each other by means of a hinge joint 4, and whereby a spring 5 is provided at the hinge joint 4.

The arms 2 and 3 are made telescopic and are formed in particular of bent far ends 6 and 7 of the above-mentioned spring 5, which can be axially moved in bent guides 8 and 9.

These guides 8 and 9 are sealed at their respective free ends 10 and 11, whereas they are open and provided with collars 14 and 15 respectively at the other far ends 12 and 13.

Further, the hinge joint 4 and the spring 5 are enveloped by a flexible capsule 16, whereby this capsule is fixed to the guides 8 and 9 over the collars 14 and 15.

In the section of FIG. 2, the construction of the hinge joint 4 and the spring 5 is represented in detail.

In the given example, the spring 5 is a double spring 5 consisting of two spiral springs 17 and 18, which are provided in a housing 19 and which are preferably made of a springy material with a cylindrical cross section, whereby this material preferably also resists the negative influences that typically occur in the oral cavity, such as for example the high humidity level and relatively high temperature, as well as the presence of certain chemical substances.

In particular, the spiral springs 17 and 18 are each fixed on either side of a plate 22 of the housing 19 with one far end 20 and 21, whereby moreover the spiral springs 17 and 18 and the plate 22 are covered with two cover plates 23 and 24 of the housing 19 which are connected to one another and to the plate 22 via a screwed joint 25 through the plate 22.

In the given example, the form of the guides and of the bent far ends of the spiral springs is circular and not chosen arbitrarily, as is illustrated by means of FIG. 3.

In this FIG. 3 is indicated a first circle A, which roughly follows the curve of Spee.

This means that the circle A with radius B touches the heads 26 of the set 28 of teeth 27 of the person concerned and goes through the maxillary joint 29.

Further, the centre 30 of this circle A is situated more or less at the height of the forehead 31, just above the eye sockets 32.

The hinge point 33 of the dental prosthesis stabilizer 1 is preferably situated on this circle A at a distance B from the maxillary joint 29, whereby this distance B is preferably selected such that the hinge point 33 is situated close to the last teeth 34 of the set of teeth 28.

Further, it is made sure that the bent far end 7 of the spiral spring 18, which is designed for a lower dental prosthesis, and the accompanying guide 11 have a curvature radius which corresponds to the curvature radius of the curve of Spee of the set of teeth 28 of the person for whom the dental prosthesis is meant, which in the given example corresponds to the radius B of the circle A.

According to the invention, the hinge point 33 is first projected parallel to the connecting line C-C between the maxillary joint 29 and the centre 30 of the circle A onto the line D-D' going through the centre 30 of the circle A and which is parallel to the connecting line E-E' between the hinge point 33 and the maxillary joint 29.

From the obtained projected point 35 can then be drawn a circle F with radius B, going through the hinge point 33.

This circle F determines the course of the bent far end 7 of the spiral spring 18 and the guide 9.

The far end 11 of the guide 9 is preferably situated at about a distance G from the hinge point 33 which corresponds to the distance G between the maxillary joint 29 and the hinge point 33.

Further, the bent far end 6 of the spiral spring 17, which is designed for an upper dental prosthesis, and the accompanying guide 8 are formed such that they mainly describe a circumference H which is formed of a circle H having the far end 11 of the guide 9 as a centre, and a radius G.

The far end 10 of the guide 8 is preferably situated on the vertical I-I' through the far end 11 of the guide 9.

The use of a dental prosthesis stabilizer 1 according to the invention is simple and is illustrated by means of FIGS. 4 and 5.

In these figures, two dental prosthesis stabilizers 1, of which only one specimen is shown for the sake of simplicity, are provided on a dental prosthesis 36, which consists of an upper dental prosthesis 37 and a lower dental prosthesis 38, and whereby the dental prosthesis stabilizers 1 form the connection between the upper dental prosthesis 37 and the lower dental prosthesis 38.

This can be done by providing or boring holes in the respective parts 37 and 38 of the dental prosthesis 36 which make it possible to provide and fix the guides 8 and 9 in the parts 37 and 38 of the dental prosthesis 36, for example by means of gluing.

The flexible capsule 16 connects to the above-mentioned open far ends 12 and 13 of the guides 8 and 9, such that the mechanism as a whole consisting of the housing 19 with the spiral springs 17 and 18 therein is screened off the oral cavity.

FIGS. 4 and 5 represent the dental prosthesis 36 in the open and closed position respectively, whereby during the opening and closing of the dental prosthesis 36, the bent far ends 6 and 7 move to and fro in the guides 8 and 9.

Thanks to the bent shape of the guides 8 and 9, as described in detail above, practically no friction will occur during said movement.

It is also clear that the spiral springs 17 and 18 exert a force with which the upper dental prosthesis 37 and the lower dental prosthesis 38 are pushed away from each other.

This force is only meant to prevent the parts 37 and 38 of the dental prosthesis 36 to become detached from the jaws, whereby this force is rather small of course, such that a person wearing a dental prosthesis 36, equipped with a dental prosthesis stabilizer 1, is not bothered when putting his teeth on top of one another.

Further, it is clear that a dental prosthesis stabilizer 1 according to the invention offers the above-mentioned advantages by comparison with the known dental prosthesis stabilizers, namely that only very few components are required to compose the dental prosthesis stabilizer 1, whereas no leavings can stay behind parts of the dental prosthesis stabilizer 1 thanks to the flexible capsule 16.

Further, the dimensions of a dental prosthesis stabilizer according to the invention are preferably restricted and adjusted to the use in the oral cavity, whereby for example the hinge point 4 is about the size of a tooth 27 at the most, so that the person wearing a dental prosthesis 36, provided with said dental prosthesis stabilizer 1, is not bothered by its presence.

A dental prosthesis stabilizer 1 may also have all sorts of other shapes than in the example shown.

Thus, it is not excluded to realize the above-mentioned spring 5 as a single spring.

Nor must the flexible capsule 16 necessarily be a separate part, but it may for example be an integrated part of the guides 8 and 9.

Moreover, the bent far ends 6 and 7, as well as the guides 8 and 9 may have other shapes than the above-mentioned circular shapes in order to obtain for example even better friction characteristics as the bent far ends 6 and 7 move to and fro in the guides 8 and 9.

The present invention is by no means restricted to the embodiment given as an example and represented in the accompanying drawings; on the contrary, such an improved dental prosthesis stabilizer may have all sorts of shapes and dimensions while still remaining within the scope of the invention.

The invention claimed is:

1. An improved dental prosthesis stabilizer having an upper arm and a lower arm connected to each other by a hinge joint and with which an upper dental prosthesis and a lower dental prosthesis are coupled to one another, wherein a spring is provided at the hinge joint with which the upper prosthesis and the lower prosthesis are pushed away from each other, wherein the upper arm is telescopic and is formed of an upper bent distal end of the spring in connection to the upper dental prosthesis and the lower arm is telescopic and is formed of a lower bent distal end of the spring in connection to the lower dental prosthesis, wherein at least the lower arm is axially movable in a lower bent guide, wherein the lower bent guide is, either fixed on the lower dental prosthesis or is embedded in the lower dental prosthesis, wherein the lower bent distal end of the spring corresponding to the lower dental prosthesis and the lower bent guide associated with the lower dental prosthesis have a curvature radius (B) that corresponds to a curvature radius (B) of the Curve of a Spee (A) of a set of teeth of a person for whom the dental prosthesis is designed.

2. The dental prosthesis stabilizer according to claim 1, wherein the upper arm is axially movable in an upper bent guide, wherein the upper bent guide is either fixed on the upper dental prosthesis or is embedded in the upper dental prosthesis, wherein the upper bent distal end of the spring corresponding to the upper dental prosthesis and the upper bent guide associated with the upper dental prosthesis have a curvature radius (G) which is equal to a difference in distance (G) between a hinge point of the dental prosthesis stabilizer and a maxillary joint of the person for whom the dental prosthesis is designed.

3. The dental prosthesis stabilizer according to claim 1, wherein the hinge joint and the spring are enveloped by a flexible capsule.

4. The dental prosthesis stabilizer according to claim 3, wherein both the upper arm and the lower arm are telescopic in the form of the upper and a lower bent distal end of the spring, respectively, and wherein the upper arm is axially movable in an upper bent guide and the lower arm is axially movable in the lower bent guide, and wherein each of the upper and lower bent guides are sealed at free ends thereof, and wherein the flexible capsule is fixed over open ends of the upper and lower bent guides.

5. The dental prosthesis stabilizer according to claim 4, wherein each of the guides is part of the flexible capsule.

6. The dental prosthesis stabilizer according to claim 2, wherein the hinge point of the dental prosthesis stabilizer has a size approximating a size of a tooth of the person for whom the dental prosthesis is designed.

* * * * *